United States Patent [19]
Cooker et al.

[11] Patent Number: 5,527,436
[45] Date of Patent: Jun. 18, 1996

[54] AKYLENE OXIDE PRODUCTION

[75] Inventors: Bernard Cooker, Malvern; Robert N. Cochran, West Chester, both of Pa.

[73] Assignee: ARCO Chemical Technology, L.P., Greenville, Del.

[21] Appl. No.: 534,571

[22] Filed: Oct. 23, 1995

Related U.S. Application Data

[63] Continuation-in-part of Ser. No. 342,501, Nov. 21, 1994, abandoned.

[51] Int. Cl.$^6$ .................... C25B 3/00; C25B 3/02
[52] U.S. Cl. ........................................... 204/428
[58] Field of Search .................. 205/428, 439, 205/455; 204/78, 79, 80

[56] References Cited

U.S. PATENT DOCUMENTS

| | | | |
|---|---|---|---|
| 3,351,635 | 11/1967 | Kollar | 260/348.5 |
| 3,427,235 | 2/1969 | Leuduc | 205/428 |
| 3,497,431 | 2/1970 | Kronig et al. | 205/428 |
| 3,635,803 | 1/1972 | Binns et al. | 205/428 |
| 3,723,264 | 3/1973 | Leduc et al. | 205/428 |
| 4,119,507 | 10/1978 | Simmrock et al. | 205/428 |
| 4,270,995 | 6/1981 | Goodridge et al. | 205/347 |
| 4,634,506 | 1/1987 | Novak et al. | 205/428 |

FOREIGN PATENT DOCUMENTS

| | | |
|---|---|---|
| 6220033 | 8/1994 | Japan . |
| 1201928 | 8/1970 | United Kingdom . |
| 1467864 | 3/1977 | United Kingdom . |

OTHER PUBLICATIONS

Holbrook, et al., "Electrooxidation of Olefins at a Silver Electrode", Journal of Catalysis, 38, pp. 294–298 (1975). no month.

Van der Eijk, et al., "Electrochemical Epoxidation of Olefins", Catalysis Today, 3, pp. 259–266 (1988). no month.

Oduoza, et al., "Aspects of the Direct Electrochemical Oxidation of Propylene", Chem. Eng. Symp. Series, 127, pp. 37–47. (no month, 1994).

Chou, et al., "Anodic Oxidation of Propylene on a Screen Electrode", Chem. Eng. Sci., 35, pp. 1581–1590 (1980). no month.

Scott, et al., "Pilot Scale Electrosynthesis of Alkene Oxides by Direct and Indirect Oxidation in a Sieve Plate Electrochemical Reactor", Chem. Eng. Sci., 47, No. 9–11, pp. 2957–2962 (1992). no month.

Otsuka, et al., "Simultaneous Epoxidation of 1–Hexene and Hydroxylation of Benzene During Electrolysis of Water", Chemistry Letters, pp. 1861–1864 (1994). no month.

Otsuka et al, "Electrocatalytic Synthesis of Propylene Oxide during Water Electrolysis", Journal of Catalysis, 157 pp. 450–460 (no month 1995).

*Primary Examiner*—John Niebling
*Assistant Examiner*—Edna Wong
*Attorney, Agent, or Firm*—William C. Long

[57] ABSTRACT

The invention relates to the electrochemical production of alkylene oxides and particularly to a process wherein an alkylene oxide is produced at both the anode and cathode of an electrochemical reactor.

10 Claims, 8 Drawing Sheets

AKYLENE OXIDE PRODUCTION

RELATED APPLICATIONS

This application is a continuation-in-part of application Ser. No. 08/342,501, filed Nov. 21, 1994 now abandoned.

BACKGROUND OF THE INVENTION

1. Field of the Invention

The present invention relates to the electrochemical production of alkylene oxides and particularly to a process wherein an alkylene oxide is produced at both the anode and cathode of an electrochemical reactor.

2. Description of the Prior Art

The production of alkylene oxide is of very great commercial importance. Ethylene oxide is produced commercially by the silver catalyzed vapor phase oxidation of ethylene with molecular oxygen.

Propylene oxide is produced commercially by the catalytic reaction of propylene with an organic hydroperoxide, see basic U.S. Pat. No. 3,351,635, or by the chlorohydrin process technology.

Research continues in an effort to develop still further improved processes for the production of alkylene oxides, and there have been efforts to apply electrochemical reaction procedures to alkylene oxide production. For example, U.S. Pat. No. 3,427,235 describes the electrochemical production of olefin oxides in an electrochemical cell by passing current through an aqueous medium to generate oxygen with the thus generated oxygen reacting with olefin to produce the oxirane compound.

U.S. Pat. No. 3,635,803 relates to the production of propylene oxide by electrochemical means using an aqueous medium containing an acetate as electrolyte.

U.S. Pat. No. 3,723,264 relates to electrochemical oxidation of an olefin using a diaphragm-compartmented electrolytic cell with an asbestos diaphragm.

U.S. Pat. No. 4,119,507 relates to electrochemical oxidation of an olefin using an aqueous alkali metal chloride electrolyte with olefin chlorohydrin formation.

UK Patent 1,467,864 relates to electrochemical oxidation of propylene to propylene oxide in an undivided cell having an aqueous solution of water soluble chloride or bromide. Electrode spacing is 0.05 to 2 mm and current densities of 1 to 100 A/dm$^2$ are used.

U.S. Pat. No. 3,497,431 relates to electrochemical production of olefin oxides in an electrochemical cell with the anode and cathode separated by an interposed diaphragm with the hydrostatic pressure in the anode compartment higher than that in the cathode compartment.

U.S. Pat. No. 4,634,506 relates to electrochemical oxidation of olefin to olefin oxide where aqueous electrolyte and olefin are mixed under pressure and are passed through a restriction device to reduce pressure and vaporize the olefin.

U.S. Pat. No. 4,270,995 relates to an electrochemical cell having an upper and lower chamber divided by a perforated plate suitable for the production of propylene oxide.

Holbrook, et al., "Electrooxidation of Olefins at a Silver Electrode", Journal of Catalysis, 38, p. 294–298 (1975) describe the electrochemical oxidation of olefins to olefin oxides.

Van der Eijk, et al., "Electrochemical Epoxidation of Olefins", Catalysis Today, 3, p. 259–266 (1988) describe the oxidation of olefins to epoxides by reaction of olefins with electrochemically generated silver (II)—pyridine ions.

Oduoza, et al., "Aspects of the Direct Electrochemical Oxidation of Propylene", Chem. Eng. Symp. Series, 127, p. 37–47 (1992), describe the direct anodic oxidation of propylene to propylene oxide and glycol in an alkaline electrolyte in batch and sieve plate bipolar flow cells.

Chou, et al., "Anodic Oxidation of Propylene on a Screen Electrode", Chem. Eng. Sci, 35, p 1581–1590 (1980) describe the oxidation of propylene to propylene oxide on a screen anode in aqueous solution of a pH of 12.0–13.9.

Scott, et al., "Pilot Scale Electrosynthesis of Alkene Oxides by Direct and Indirect Oxidation in a Sieve Plate Electrochemical Reactor", Chem. Eng. Sci., 47, No. 9–11, p. 2957–2962 (1992), describes the electrosynthesis of alkene oxides in a sieve plate electrochemical reactor.

Japanese Kokai No. 6-220033 describes the production of alkylene oxides from olefin and oxygen through the use of a fuel cell system with hydrogen fed to the anode chamber and olefin and oxygen fed to the cathode chamber. Alkylene oxide is produced in the cathode chamber.

Otsuka, et al., "Simultaneous Epoxidation of 1-Hexene and Hydroxylation of Benzene During Electrolysis of Water", Chemistry Letters, p. 1861–1864 (1994) describe a system for simultaneous epoxidation of 1-hexene at the anode and the hydroxylation of benzene at the cathode during the electrolysis of water. Otsuka also anodically epoxidized cyclohexene in a fuel cell system, the oxygen being abstracted from water at the anode. The highest current efficiency was 4.5%, at 47.6% selectivity to the epoxide. The cathode chemistry is proton reduction to hydrogen gas. See "Epoxidation of Cyclohexene with the Nascent Oxygen Generated by electrolysis of Water", K. Otsuka, M. Yoshinaka and I. Yamanaka, J. Chem. Soc., Chem. Commun., (1993), p. 611–612. Oxidation of toluene to benzaldehyde by Mn$^{3+}$ and OH free radicals, generated in the anodic and cathodic reactions, respectively, was carried out simultaneously in the cathodic and anodic compartments of a cell. The selectivity of benzaldehyde was very high in both the anodic and cathodic reactions. The maximum total current efficiency for benzaldehyde production in the paired electrooxidation was 171%. See "Paired Electrooxidation. I. Production of Benzaldehyde", J. J. Jow, A. C. Lee, T. C. Chou, J. Appl. Electrochem., vol, 17, (1987), p. 753–759.

In hydrogen peroxide production, the consumption of anode by product oxygen at the cathode is known. See for example, "Processes for the Production of Mixtures of Caustic soda and Hydrogen Peroxide via the Reduction of Oxygen", P. C. Foller, R. T. Bombard, J. of Applied Electrochemistry, vol. 25 (1995). p. 613–627.

BRIEF DESCRIPTION OF THE INVENTION

In prior procedures, alkylene oxide was produced at one reactor electrode and a product generally of much less value at the other. Now, in accordance with the present invention, an electrochemical process is provided whereby alkylene oxide is produced at both electrodes of the electrochemical reactor. At the anode, there is electrolysis of water with the formation of oxygen which is reacted with olefin fed to the anode chamber to form alkylene oxide. At the same time, olefin and oxygen are fed to the cathode chamber along with protons which are formed at the anode and transported to the cathode and these materials are reacted in the cathode chamber to also form alkylene oxide.

DESCRIPTION OF THE DRAWING

The accompanying drawings illustrate various practices of the invention.

DETAILED DESCRIPTION

In accordance with the present invention, an electrochemical reactor is provided having an anode and a cathode and having proton transfer means by which protons formed at the anode are transferred to the cathode. A mixture of olefin and oxygen is fed to the cathodic zone and olefin is fed to the anodic zone. Aqueous electrolyte is fed to the electrochemical reactor and electrolysis of water is carried out at the anode with formation of protons and oxygen. Oxygen thus formed is believed to react directly with olefin in the anodic zone to form alkylene oxide product. Protons formed by the water electrolysis are efficiently transferred to the cathode zone to which is also introduced olefin and oxygen, and these components react to form alkylene oxide in the cathode zone.

While not wishing to be bound by theory, it is believed that protons and oxygen react at the cathode to form hydrogen peroxide, or peroxide ion or a hydroperoxide of a metal of the cathode and this peroxide reacts further with olefin to form alkylene oxide. It should be noted that materials such as titanium silicalite, generally zeolites containing titanium atoms, of the following general formula: $xTiO_2(1-x)SiO_2$, when incorporated in or coated on the cathode, or otherwise added to the cathode zone markedly enhance the alkylene oxide production therein.

Figure 1:
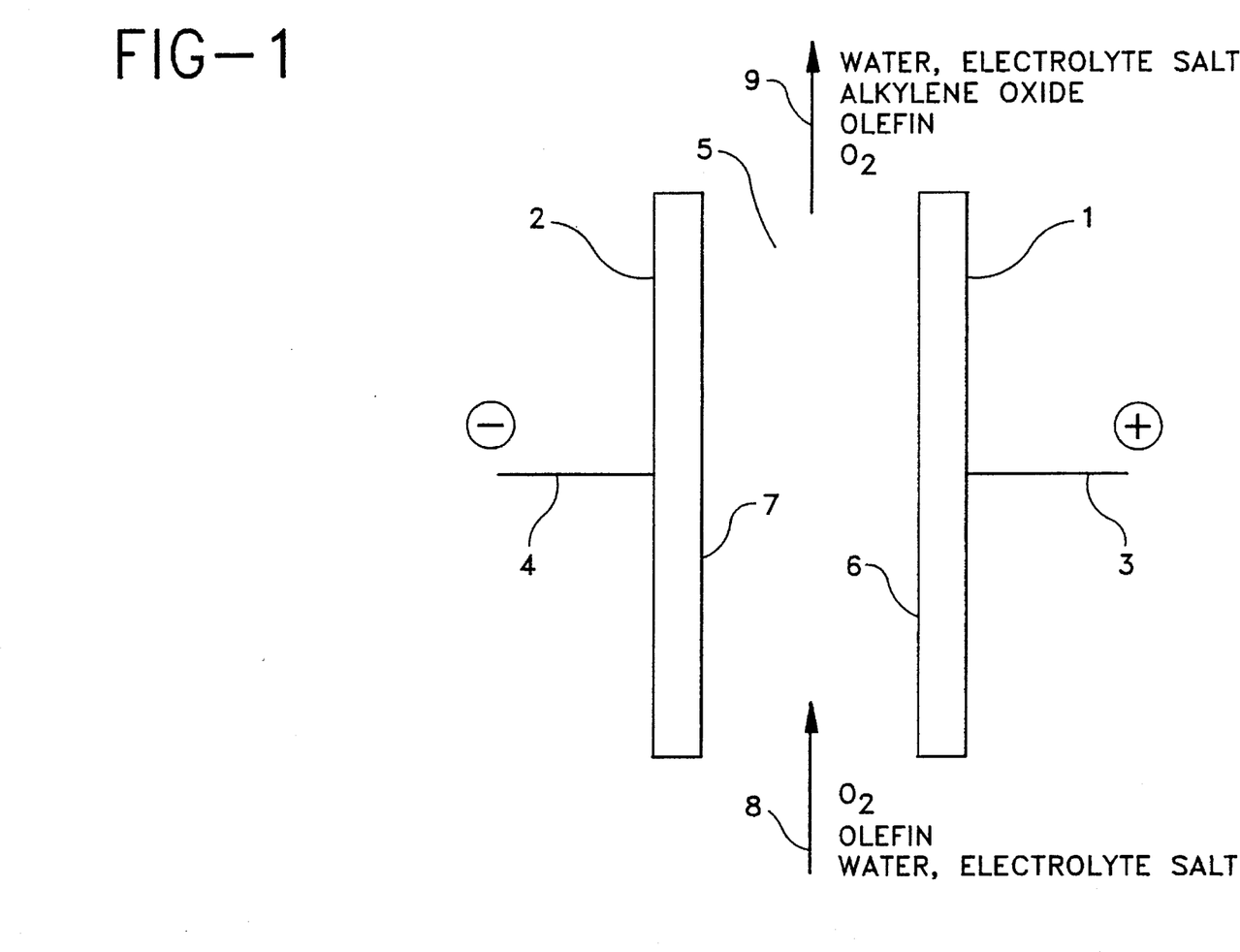
FIG. 1 is a simple schematic illustrating the invention.

Referring to FIG. 1, there are provided anode 1 and cathode 2 to which is applied a potential difference by means of connections 3 and 4. Separate anodic and cathodic chambers can be provided but for purpose of simplicity only one zone 5 is represented between the anode and cathode. A mixture comprised of olefin, oxygen, electrolyte salt and water, the latter appropriately in the form of an aqueous electrolyte, is fed to zone 5 via means 8.

At the anodic surface 6, water electrolysis takes place with the formation of protons ($H^+$) and oxygen, and the liberation of electrons. Oxygen thus formed reacts in the vicinity of the anodic surface with olefin to form alkylene oxide.

At the same time, protons formed at the anodic surface are transferred across zone 5, for example via the aqueous electrolyte, to cathodic surface 7 where a reaction occurs between the oxygen fed via means 8 and the protons from anodic surface 6 as well as the olefin fed via means 8 with the formation in the vicinity of cathodic surface 7 of alkylene oxide. While not wishing to be bound by theory, it is believed that the cathodic surface reaction first involves reaction of oxygen, protons and electrons to form hydrogen peroxide or a peroxide ion or a hydroperoxide of a metal of the cathode and that the peroxide in turn reacts with olefin to form alkylene oxide.

Alkylene oxide formed at both the anode and cathode exits zone 5 via means 9 to recovery. Other components such as oxygen, olefin, water and the like can be separated and recycled.

Practice of the invention is applicable generally to the epoxidation of olefins to alkylene oxides. Preferred olefins are those having from about 2 to 30 carbon atoms. Illustrative olefins are ethylene, propylene, normal butylene, isobutylene, the pentenes, the methyl pentenes, the normal hexenes, the octenes, the dodecenes, cyclohexenes, methyl cyclohexene, butadiene, styrene, methyl styrene, vinyl toluene, vinylcyclohexene, the phenyl cyclohexenes, and the like. Olefins having halogen, oxygen, sulfur and the like containing substituents can be used. Such substituted olefins are illustrated by allyl alcohol, methyallyl alcohol, cyclohexenol, diallyl ether, methyl methacrylate, methyl oleate, methyl vinyl ketone, allyl chloride, and the like. In general, all olefinic materials epoxidized by methods previously employed can be epoxidized in accordance with this process.

The lower olefins having about 2 to 4 carbon atoms in an aliphatic chain are advantageously epoxidized by this process. The class of olefins commonly termed alpha olefins or primary olefins are epoxidized in the particularly efficient manner by this process.

It should be noted that where the same olefin is fed to both the anodic and cathodic zones, the alkylene oxide formed in each zone will be the same. A feature of the invention, however, is that where different olefins are fed to the anodic and cathodic zones, different alkylene oxides will be produced. Thus it is possible, for example, to produce simultaneously the two most important alkylene oxides, ethylene oxide and propylene oxide by practice of the invention.

The cathodes can consist of a mixture of a macromolecular solid which flows under suitable conditions of heat and pressure, to act as a binder, and a metal, where the metal is in Group 8, 9 or 10 of the periodic table. An example of a suitable macromolecular binder is Teflon resin powder and palladium black (palladium powder) is a suitable catalytic metal in the cathode. The component powders are mixed and subjected to heat and pressure to form a flat porous plate of suitable dimension and strength. The cathodes may also consist of a metal, where the metal is in Group 8, 9, or 10 of the periodic table, without the inclusion of a binder and be formed as a solid or porous sheet. Alternatively, the cathode may be carbon or carbon in a Teflon matrix, for example. The cathodes may also be a mixture or carbon and a metal from Group 8, 9, or 10 of the periodic table. The cathodes may be in the form of solid plates, porous sheets foams or meshes. The anodes can be prepared from electrodes known to facilitate direct anodic oxidation. These include 304 and 316 stainless steel, nickel, silver, graphite/silver mixture, silver oxide/silver mixture, titanium, ruthenium oxide on titanium, iridium oxide coated Ebonex, platinized titanium and glassy carbon. They can also be copper, cobalt, or spinels, specifically nickel/cobalt ($NiCoO_2$) coated on titanium. These can be used as solid plates, porous sheets, reticulated metal, foams or meshes. Specific instances of particularly advantageous anode and cathode materials, in particular geometrical forms are given in the examples below. The anode can be improved in its efficiency in producing propylene oxide by applying cathodic, negative voltage of a value which is at least sufficient for hydrogen gas discharge continuously for at least a few seconds and preferably up to 40 minutes. The anode is also in the case of nickel advantageously improved in its efficiency in forming propylene oxide, treated by cathodically electroplating nickel hydroxide onto its surface.

The electrolyte can consist of oxygen-containing inorganic salts of general formula $Z_dW_aX_bY_c$, where a, b and c are positive integers, d is a positive integer or zero, W is an alkali metal, or an alkaline earth metal, X is molybdenum, tungsten, chromium, zinc, bismuth, antimony, vanadium, tellurium, selenium, aluminum, tin, silicon, phosphorus, boron or sulfur, Y is oxygen and Z is hydrogen. The element X is preferably in its highest oxidation state, rendering it inert to anodic oxidation.

Another class of electrolytes which may be used are the water soluble salts of organic acids, where the cation is alkali metal, alkaline earth, cobalt, thallium, nickel or silver and the anion is chosen from citrate, oxalate, gluconate, benzoate, phthalate, formate or acetate.

Electrolytes can also consist of the hydroxides of alkali metals or alkaline earths.

Mixtures of two or more such electrolytes may be used. In principle, any electrolyte pH may be used but in practice the electrolyte is preferably neutral or mildly basic ($6.9 < pH < 11$). Lower pHs are more corrosive to metallic electrodes, vessels and other components and higher pHs accelerate the hydrolysis of propylene oxide to the glycol. Examples of satisfactory electrolyte are aqueous solutions of tripotassium phosphate, dipotassium monohydrogen phosphate, disodium monohydrogen phosphate, mixtures of phosphoric acid and tripotassium phosphate within the pH range 6.9 to 11.0 and the sodium equivalents. Halides, particularly iodide, bromide, and chloride are not suitable in the direct anodic electrochemistry, because the elemental halogen can discharge at the anode in preference to oxygen.

Relatively mild, reaction conditions can be employed, illustrative temperatures are 0° to 200° C. with 10° to 100° C. being preferred, and illustrative pressures are 15 to 500 psia.

It is especially advantageous to employ a water miscible organic propylene solubilizing agent with the electrolyte to aid in propylene solubilization. Tertiary alcohols having 4–12 carbon atoms, especially tertiary butyl alcohol, are suitable.

For industrial application, a bipolar stack reactor system is preferred but monopolar arrays also function efficiently. The cathodes consist of a mixture of a macromolecular solid which flows under suitable conditions of heat and pressure, to act as a binder, and a metal, where the metal is in Group 8, 9 or 10 of the periodic table. An example of a suitable macromolecular binder is Teflon resin powder and palladium black (palladium powder) is a suitable metal in the cathode. The component powders are mixed and subjected to heat and pressure to form catalytic metal cathode material. The component powders are mixed and subjected to heat and pressure to form a flat plate of suitable dimensions and strength. The cathodes may also consist of a metal where the metal is in Group 8, 9, or 10 of the periodic table, without the inclusion of binder and be formed as a solid or porous sheet. Alternatively the cathodes may be carbon or a carbon Teflon matrix, or other materials. The cathodes may also be a mixture of carbon and a metal from Group 8, 9, or 10 of the periodic table. The anodes can be prepared from electrodes known to facilitate direct anodic oxidation. These include 304 and 316 stainless steel, nickel, silver, graphite/silver mixture, silver oxide/silver mixture, titanium, ruthenium oxide on titanium, iridium oxide coated Ebonex, platinized titanium and glassy carbon. The electrochemical reactor consists of a stack of parallel electrode elements and associated gas feed channels, numbering between 50 and 500, mounted inside a pressure vessel which is internally coated with polymer or other substance which is electrically insulating and chemically resistant to the electrolyte deployed. The gap between the electrode faces is uniform and in the range 2 to 10 mm. Each element of the stack consists of an anode and a cathode, which are mechanically and electrically bonded to each other; each anode/cathode pair is oriented in the same direction across the stack. The electrodes are between 2 and 20 mm thick, depending on the demands of mechanical strength, conduction and intra-electrode diffusion of gas and/or liquid. The plates are between 1 and 10 m in length and preferably 2 to 4 m in this dimension. Electrically insulating spacers, for instance of polypropylene, polyethylene or other inert, formable, low cost material, may be placed between the plates at appropriate intervals, to maintain the electrode separation. These spacers occupy less than 50% and preferably less than 10% of the electrolyte flow cross-sectional area.

The electrodes are parallel to the axis of the cylindrical vessel and the bipolar stack is square in cross section. The inside diameter (ID) of the containing vessel is 1.5 times the electrode plate width, to minimize the vessel size which accommodates the stack. A 2 m width plate is accommodated most efficiently in a 3 m ID vessel. The most economical ratio of containing vessel tangent to tangent length (TTL) to ID is usually 2/1 to 4/1. Thus electrodes which are 4 m in length are 0.67 m to 1.33 m in width. The electrodes extend in height from the lower tangent line of the vessel to the upper tangent line of the vessel.

The edges of each electrode are electrically insulated using strips of polypropylene, polyethylene or other inert, formable and low cost material. The volume between the electrode stack and the vessel wall, over the height of the plates, is filled with the same electrically insulating material as is applied to the edges of the electrode plates. This insulation eliminates all electrical current, except that between the faces of the electrodes. It also ensures that all fluid flow is between the electrodes, where the electrochemistry is conducted.

The containing vessel has a detachable lid of standard profile, permitting installation and removal of the electrode stack, insulation and other vessel contents.

The spaces between the electrodes are filled with flowing aqueous electrolyte, which is pumped into the base of the reactor through a flow distributor, which provides uniform fluid flux into the bipolar stack. It exhausts, with the process gases, from the top of the vessel. The flow rate is such that the electrolyte mean velocity in the electrode gaps is 0.1 to 5 ft/s and preferably 1 to 5 ft/s. The liquid electrolyte consists of an aqueous solution of a salt which is chemically inert under the process conditions and which provides adequate electrical conductivity. The exception is the use of metal hydroxide electrolytes, where the hydroxide is oxidized to oxygen at the anode. The concentration of solute is typically between 0.1 and 50 wt % or a high fraction of the saturation concentration, whichever is lower. Electrolytes as described above are used.

Where propylene oxide is the desired product, a gaseous mixture of propylene and oxygen gas is fed to the reactor through a gas distributor, which is located below the electrode stack and which provides a uniform flux of gas over the cross-section of the stack. The gas and liquid flow concurrently through the stack. The oxygen dissolved in the electrolyte undergoes no anodic reaction and reacts with protons at the cathode, yielding hydrogen peroxide or cathode metal hydroperoxide which is consumed by the propylene, forming propylene oxide and water. Propylene reacts at the anode with the oxygen which is liberated there from water. The propylene is present in sufficient concentration in the gas phase to maintain a fuel-rich, nonflammable atmosphere. The electrolyte, propylene oxide and residual gas flow from the reactor and the propylene oxide is separated by distillation or other means. The bipolar stack is electrified by the application of 0.5 to 5V per electrode pair, with the appropriate polarity, at the outermost electrodes and bipolarity is induced across all the intervening electrodes.

The reactor preferably operates at between 30° and 70° C. and the pressure of operation must be above that at which the electrolyte boils. Pressure promotes the solubility of propylene and oxygen reactants in the electrolyte and reduces the volume fraction of gas in the mixture. Promotion of the liquid phase oxygen and propylene concentration permits higher current densities to be used and compression of the vapor volume increases the specific electrical conductivity of the two-phase mixture in a direct linear manner. The reactor is operated above 45 psig and below 135 psig if gaseous propylene is employed.

The following examples illustrate the invention.

Example 1—Bipolar Stack Array/Flowing Electrolyte

Figure 2:
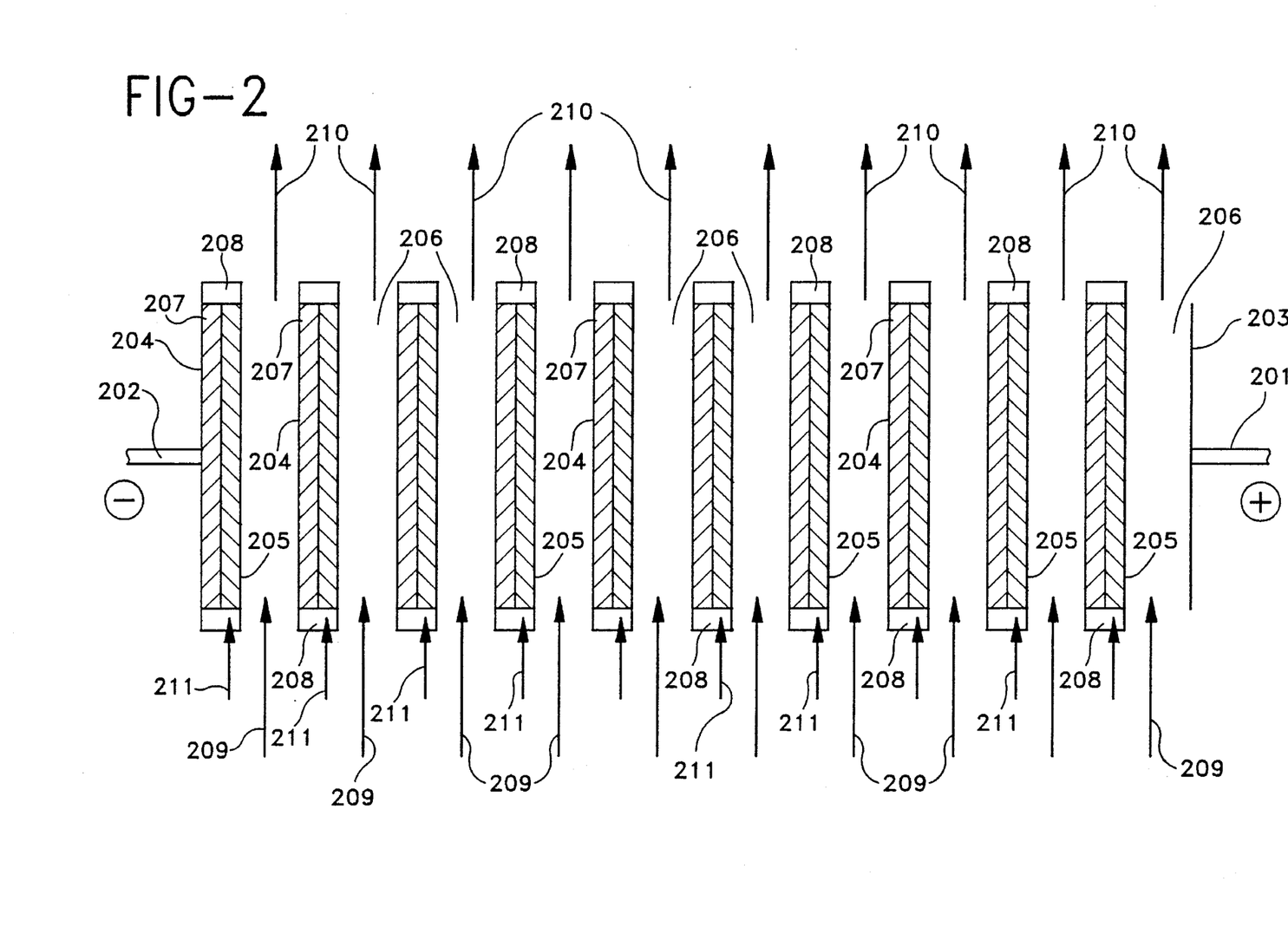
FIG. 2 illustrates practice of the invention using a bipolar stack array reactor, with cathode propylene/oxygen feed between the anode and the cathode.

FIG. 2 illustrates practice of the invention with a bipolar stack array and continuously flowing electrolyte. Referring to FIG. 2, electrical connections 201 and 202 are provided which are connected respectively to an external positive DC terminal and an external negative DC terminal. Externally polarized 304 stainless steel plate 203 is provided which is 3 mm thick, 3 ft. long and 3 ft. wide.

Each bipolar unit comprises a 304 stainless steel plate anode 204 which is 3 mm thick, 3 ft. long and 3 ft. wide and a cathode 205 which is formed by hot pressing a 99% by weight palladium and 1% by weight teflon mixture to a dimension 1 mm thick, 3 ft. long and 3 ft. wide. Liquid electrolyte flow channels 206 are provided 2 mm wide.

Gas flow channels 207 are provided 5 mm wide containing 304 stainless steel electrically conducting mesh with 25% open area parallel to electrode faces tacked to anode and cathode. The bipolar stack is surrounded by solid polypropylene insulation between the lower and upper edges of the stack. Polypropylene electrical insulation 208 is provided as a 9 mm wide by 9 mm wide strip around the entire bipolar electrode perimeter with the lower edges slotted for cathode gas feed.

Every plate of the reactor is polarized through polarization of the electrodes at the outside of the stack.

A mixture of 75 vol % propylene and 25 vol % oxygen is fed to the gas flow channels 207 via 211.

The flowing electrolyte is introduced into channels 206 via 209 flowing therethrough in an upwardly direction. The electrolyte is 5 wt % disodium hydrogen phosphate in water, saturated with propylene; it is pumped through the electrode stack at 3 ft/s to promote rapid mass transfer and minimize the mean residence time of the propylene oxide product, minimizing hydrolysis to propylene glycol. At each anode, water is electrolyzed and the surface-associated oxygen which forms reacts with propylene from the propylene and electrolyte mixture, yielding propylene oxide. The protons formed at the anode readily diffuse across the narrow inter-electrode gap (2 mm) to the cathode and are there reacted with oxygen and propylene at or near the gas/electrolyte/cathode interface. Propylene dissolved in the electrolyte from the feed, or that dissolved from the propylene/oxygen intra-cathode gas feed, reacts to form propylene oxide and reform the water which was consumed by electrolysis. Overall, the salt and solvent of the electrolyte are conserved. The propylene oxide product dissolves in the electrolyte and leaves the reactor with the exhaust electrolyte flow via 210 and it is removed by distillation.

The illustrated reactor design eliminates extraneous electrical fields by two means: a polypropylene electrical insulation strip 208, 9 mm by 9 mm in cross-section, runs around the perimeter of each electrode plate, eliminating current from the edges. Also, the backs of the outside electrode plates are insulated with polypropylene, eliminating current from these locations. The stack has 10 electrode pairs and is run in a corrosion-resistant pressure vessel. The temperature is 30° C. and the electrolyte is fed at 100 psig.

The reactor operates with 27.0 volts applied across the stack and the current density is 2,000 $A/m^2$. The anodes yield the following products relative the current: $O_2$ 20%, propylene oxide 76%, propylene glycol 4%. The cathodes yield the following products relative to the current: propylene oxide 80%, water 10%, oxygen 10%.

Example 2—Bipolar Stack Array with Extra-Cathode Oxygen Feed

Figure 3:
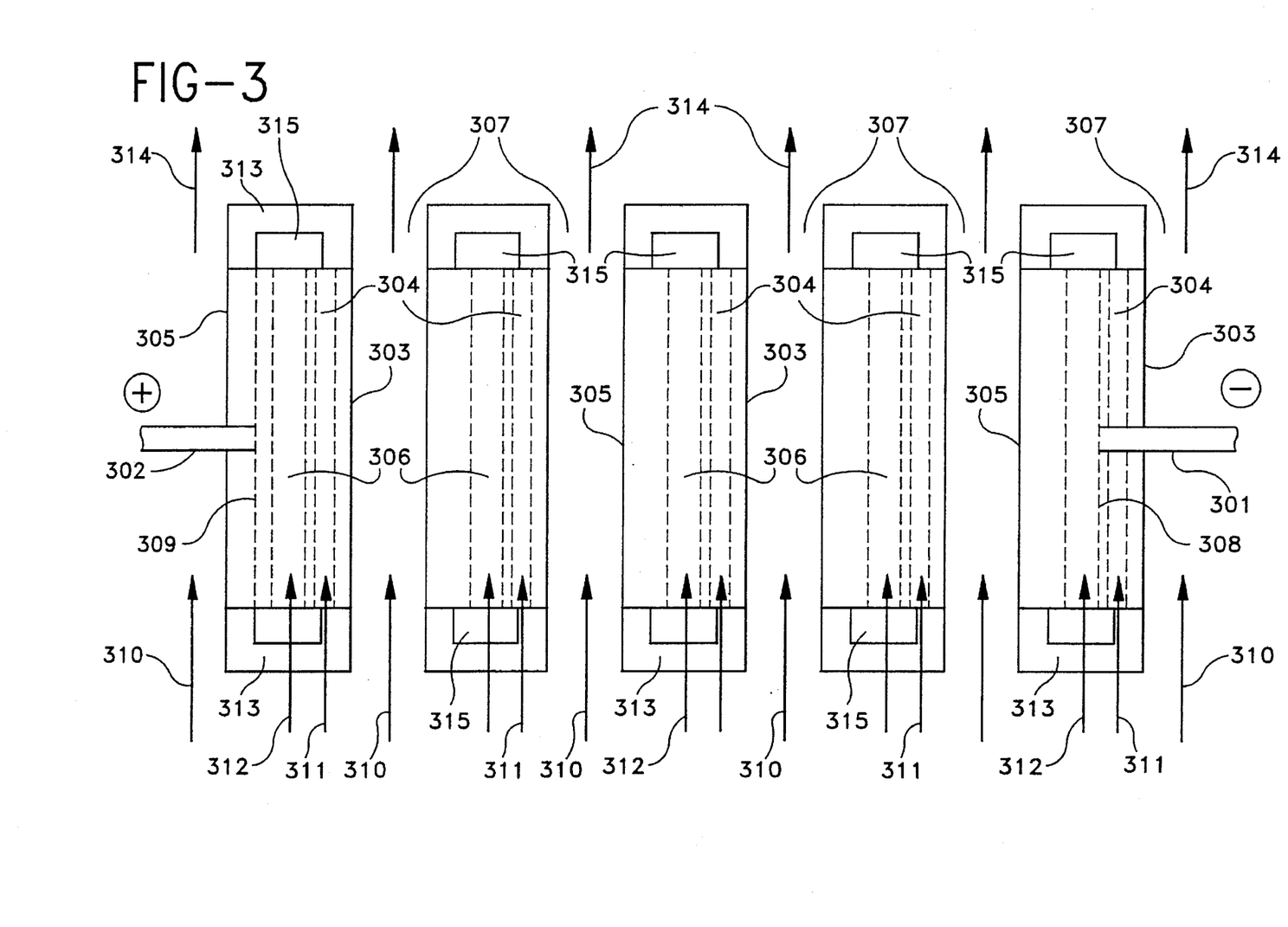
FIG. 3 illustrates practice of the invention using a bipolar stack array reactor with intra-cathode oxygen feed.

FIG. 3 illustrates practice of the invention with a bipolar stack array and extra cathode oxygen feed. In FIG. 3, electrical connections 301 and 302 are connected respectively to an external negative DC terminal and an external positive DC terminal and connected to current distribution grids 308 and 309 made of 316 stainless steel.

Cathodes 303 are provided having the same composition and dimensions as shown in FIG. 2, as further described in Example 1. Within each cathode are provided planar gas flow channels 304 which are 1 mm wide.

Anodes 305 are provided which are 304 stainless steel porous sintered metal plates 3 mm thick, 3 ft. long and 3 ft. wide. Membranes 306 are provided between the anode and cathode pairs which are glass wool 1 mm thick soaked in 5 wt % disodium hydrogen phosphate.

Propylene solution flow channels 307 are provided which are 2 mm wide, tertiary butyl alcohol solvent saturated with propylene being added via 310. Gas feed means 311 are provided for feeding a gas mixture of 75 vol % propylene and 25 vol % oxygen to the cathode gas flow channels.

Feed means 312 are provided for feeding water to the glass membrane.

The electrode stack is surrounded by solid polypropylene insulation between the lower and upper edges of the stack. Polypropylene solid electrical insulation strip 313 7 mm wide by 7 mm thick is provided around the entire perimeter of each anode/membrane/cathode unit.

The reactor system consists of a stack of 5 electrode pairs in a bipolar array, with a solution of propylene in an inert solvent flowing between them. The anodes 305 consist of sintered, porous 304 stainless steel, 3 mm thick and 3 ft. in the other dimensions. The anode and cathode 303 are separated by a membrane 306 consisting of glass wool soaked in 5 wt % disodium hydrogen phosphate, 1 mm thick. Each cathode is a porous composite, 99 wt % palladium, 1 wt % Teflon, formed by hot pressing a powder mixture, 3 mm thick and 3 ft. in the other dimensions. The cathodes have a central branched slot 304 through which gaseous propylene (75%) and oxygen (25%) are fed to the interior of the electrode. Reaction occurs on the anodes, water from the membrane being electrolyzed to surface-associated oxygen and protons. The surface-associated oxygen reacts with propylene, which is contained in the liquid feed flowing between the electrode pairs in channel 307. The liquid feed is tertiary butyl alcohol, saturated with propylene, with 20 vol % propylene/oxygen gas. The gas composition is 75 vol % propylene and 25 vol % oxygen. The mean liquid feed velocity is 3 ft/s.

The protons from the first anode reaction diffuse through the membrane to the cathode, where they are thought to react with oxygen from the cathode gas feed via 311 to yield hydrogen peroxide or a cathode metal hydroperoxide. Propylene, whether contained in the intra-cathode gas feed via 311 or dissolved in the liquid flowing between the electrodes reacts with the peroxide on the cathode surface and propylene oxide and water are formed. Although this chemistry formally yields no net consumption of water in the membrane, the membranes are subject to a slow deionized water feed at slight pressure relative to the electrodes via 312 to compensate for water lost by molecular diffusion through the electrodes into the liquid between the electrodes. The propylene oxide product dissolves in the liquid between the electrodes, and leaves the reactor with the exhaust liquid flow via 314 and it is removed by distillation. The major organic byproduct is propylene glycol, which is removed by extraction.

The edges of the electrode pairs have an electrically insulating polypropylene strip 313 on all four sides, which is 7 mm by 7 mm in cross-section, eliminating electrical discharge at the edges. Each adjacent anode and cathode is connected by a continuous 304 stainless steel strip 315 which runs around the entire perimeter of each electrode pair and which is shielded on three sides by the polypropylene strip. This provides the necessary electrical connection between the anode and cathode for the electrochemistry to proceed. The bipolar stack is polarized by the application of the DC voltage to the first and last electrodes through conductor wires 301 and 302, connected to an external source of DC voltage. The first anode and last cathode, which are externally polarized, contain a 304 stainless steel mesh, which is connected to the external conductor wire. The mesh both mechanically reinforces the electrodes and ensures uniform voltage and current density across the driven anode and cathode planes. A uniform electrical field is also dependent on the use of solid polypropylene on all four sides of the stack over its entire height. This eliminates conduction to the vessel walls.

The stack is run in a polymer-lined, corrosion-resistant pressure vessel. The temperature of the propylene solution feed is 30° C. and its pressure is 100 psig.

The reactor operates with 16.0 volts applied across the stack and the current density is 2,500 A/m$^2$. The anodes yield the following products relative to the current: $O_2$ 20%, propylene oxide 76%, propylene glycol 4%. The cathodes yield the following products relative to the current: propylene oxide 80%, water 10%, oxygen 10%.

Example 3—Bipolar Stack Array with Extra-Cathode Oxygen Feed

Figure 4:
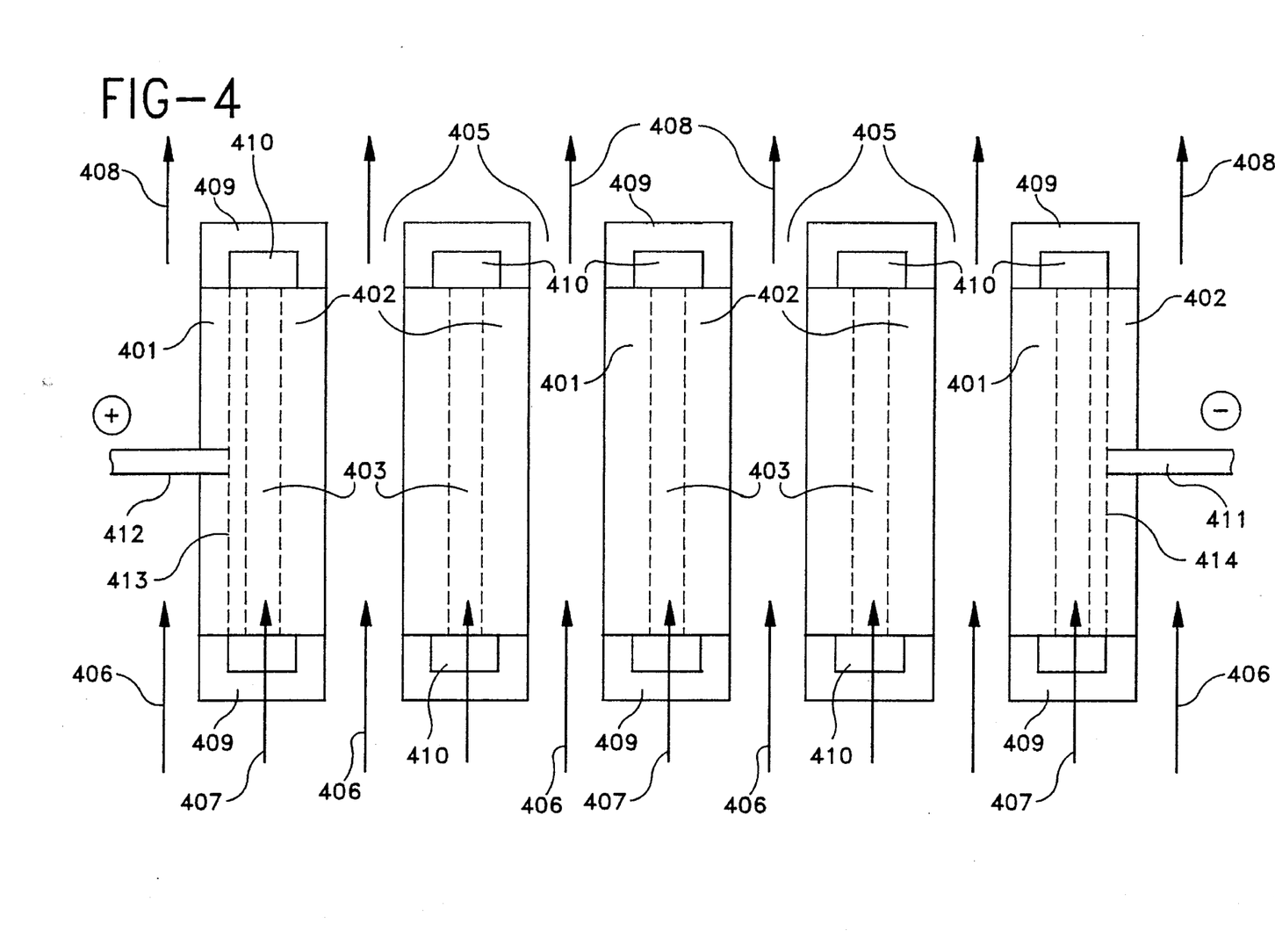
FIG. 4 illustrates practice of the invention using a bipolar stack array reactor with extra-cathode oxygen feed.

The reactor system is presented in FIG. 4. It consists of a stack of 5 electrode pairs in a bipolar array, with a propylene solution flowing between them. The anodes 401 consist of sintered, porous 304 stainless steel, 3 mm thick and 3 ft. in the other dimensions. The anode and cathode are separated by a membrane 403 consisting of glass wool soaked in 5 wt % disodium hydrogen phosphate, 1 mm thick. Each cathode is a porous composite, 99 wt % palladium, 1 wt % Teflon, formed by hot pressing a powder mixture, 3 mm thick and ft. in the other dimensions. Electrolysis of water occurs on the anodes, water from the membrane being electrolyzed to surface-associated oxygen and protons. The surface-associated oxygen reacts with propylene, which is contained in the liquid feed flowing between the electrode pairs in zone 405. The liquid feed via 405 is tertiary butyl alcohol, saturated with propylene, with 20 vol % propylene/oxygen gas cofeed. The gas is 75 vol % propylene and 25 vol % oxygen. The mean stream velocity is 3 ft/s.

The protons from the first anode reaction diffuse through the membrane 403 to the cathode where they react with oxygen, which is conveyed to the cathode as gaseous cofeed with the liquid feed via 406 which flows between the electrode pairs. Propylene, dissolved in the liquid feed, diffuses to the cathode and reacts with the peroxide formed in the cathodic region. Although the chemistry formally yields no net consumption of water in the membrane, the membranes are subject to a slow deionized water feed via 407 at slight pressure relative to the electrodes, to compensate for water lost by molecular diffusion through the electrodes into the liquid between the electrodes. The propylene oxide product dissolves in the electrolyte, leaves the reactor with the exhaust electrolyte flow via 408 and it is removed by distillation. The major organic byproduct is propylene glycol, which is removed by extraction.

The edges of the electrode pairs have an electrically insulating polypropylene strip on all four sides 409, which is 5 mm by 5 mm in cross-section, eliminating electrical discharge at the edges. Each adjacent anode and cathode is connected by a continuous 304 stainless steel strip 410 which runs around the entire perimeter of each electrode pair and which is shielded on three sides by the polypropylene strip 409. This provides the necessary electrical connection between the anode and the cathode for the electrochemistry to proceed. The bipolar stack is polarized by the application of the DC voltage to the first and last electrodes through conductor wires 411 and 412 which are connected to an external source of DC voltage. The first anode and last cathode, which are externally polarized, contain 304 stainless steel mesh 413 and 414, which is connected to the external conductor wire. The mesh both mechanically reinforces the electrodes and ensures uniform voltage and current density across the driven anode and cathode planes. A uniform electrical field is also dependent on the use of solid polypropylene on all four sides of the stack over its entire height. This eliminates conduction to the walls.

The stack is run in a polymer-lined, corrosion-resistant pressure vessel. The temperature of the propylene solution feed is 30° C. and its pressure is 100 psig.

The reactor operates with 15.0 volts applied across the stack and the current density is 2,000 A/m$^2$. The anodes yield the following products relative to the current: $O_2$ 20%, propylene oxide 76%, propylene glycol 4%. The cathodes yield the following products relative to the current: propylene oxide 80%, water 10%, oxygen 10%.

Figure 5:
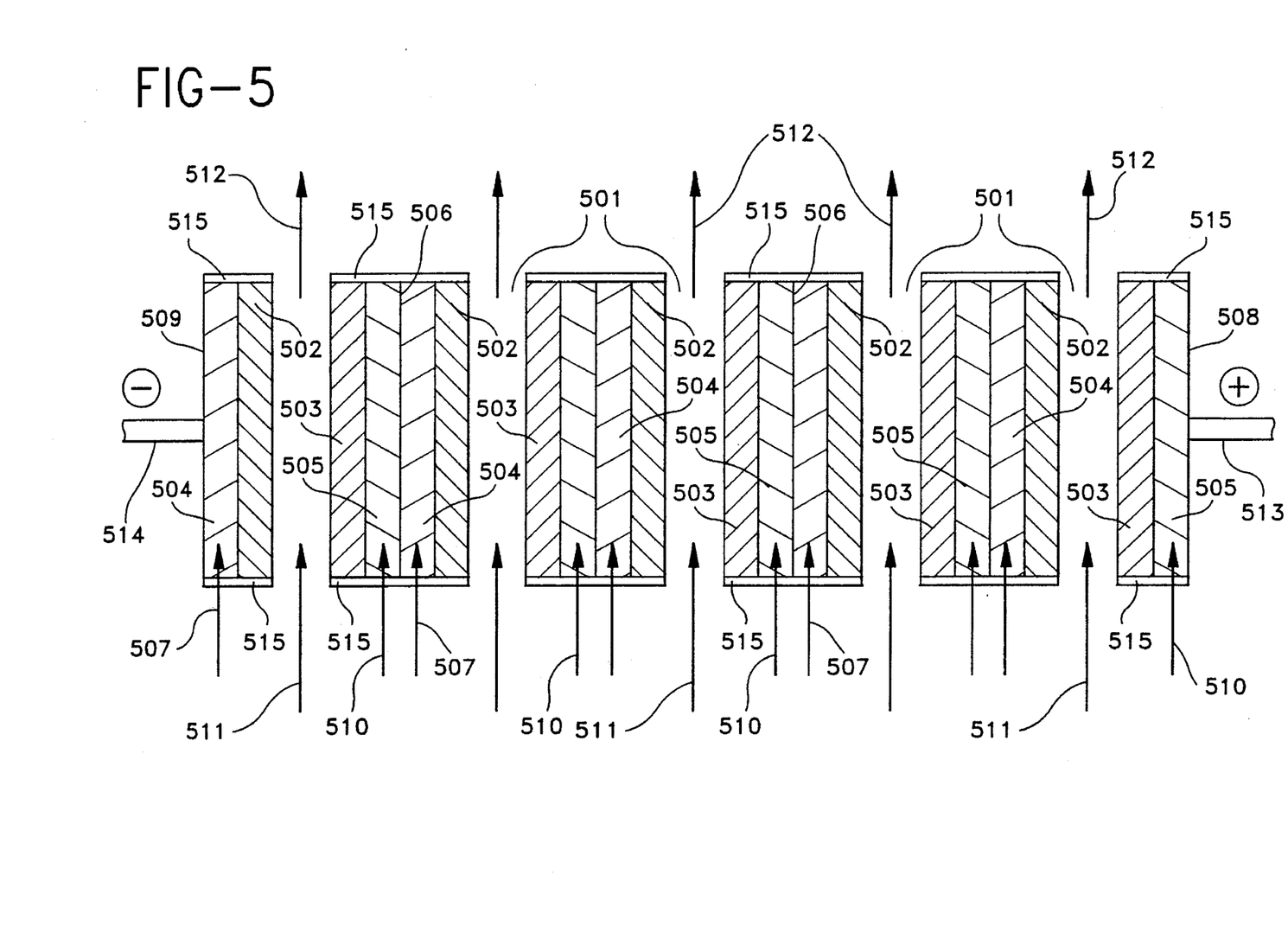
FIG. 5 illustrates practice of the invention using a bipolar stack array reactor with flowing electrolyte, olefin-permeable anodes and olefin/oxygen-permeable cathodes.

Example 4—Bipolar Stack Array/Plowing Electrolyte/Propylene-Permeable Anodes This continuous reactor system is illustrated in FIG. 5. The system comprises a stack of parallel electrodes, with electrolyte flow channels 501 between them and means to electrically polarize the stack via the electrodes at the extremities. Each unit of the electrode stack consists of a cathode 502, and anode 503, gas feed channels 504 and 505 and a partition 506 separating the gas flows. The cathodes 502 are formed by hot pressing a powder mixture of 99 wt % palladium and 1 wt % Teflon, yielding an electrically conducting, porous plate which is 1 mm thick and 3 ft. in the other dimensions. Each anode is flat plate of porous sintered 304 stainless steel, 3 mm thick and 3 ft in the other dimension. The electrodes have separate gas feeds, separated by a 3 mm thick plate of 304 stainless steel. The gas flow channel behind the cathode is 304 stainless steel mesh, 5 mm thick and of 25% open area. The channel allows oxygen (25 vol %) and propylene gas (75 vol %) fed via 507 access to the entire cathode area and the gases permeate the pores of the electrode, flowing through it towards the electrolyte flow channel 501. The metal mesh defining the cathode gas flow channel also conducts electricity between the cathode and the metal partition 506 separating the cathode and anode gas feeds. Every plate of the reactor is polarized through polarization of the electrodes at the outside of the stack. The externally polarized anode and cathode are shown as 508 and 509 in FIG. 5. The mechanical arrangement on the anode side is the same: the anode side gas channel 505 is also 5 mm thick and of 304 stainless steel, with 25% open area, which conducts electricity from the metal partition 506 separating the anode and cathode gas feed to the anode. The gas feed via 510 is 100% propylene, boosting the concentration of propylene at the anode surface.

The flowing electrolyte via 511 is 5 wt % disodium hydrogen phosphate in water, saturated with propylene; it is pumped through the electrode stack at 3 ft/s to promote rapid mass transfer and minimize the mean residence time of the propylene oxide product, minimizing hydrolysis to propylene glycol. Electrolysis of water occurs at the anode and the surface-associated oxygen which forms reacts with propylene from the electrolyte and propylene mixture and from the propylene flow behind the anode. The protons formed at the anode diffuse rapidly across the narrow (2 mm) interelectrode gap 501, to the cathode and they are incorporated in the reaction, which occurs in the cathode, at or near the gas/electrolyte/cathode interface. Propylene dissolved in the electrolyte from the feed, or that dissolved from the propylene/oxygen intra-cathode gas feed via 507, reacts with the cathodic peroxide to form propylene oxide and reform the water which was consumed. Overall, the salt and solvent of the electrolyte are conserved. The propylene oxide product dissolved in the electrolyte leaves the reactor with the exhaust electrolyte flow via 512 and it is removed by distillation.

The electrical bipolarity of the stack is induce by applying the DC voltage to the first and last electrodes of the stack through the external conducting wires 513 and 514.

The reactor design eliminates extraneous electrical fields by two means: a polypropylene electrical insulation strip 515, which is 17 mm by 17 mm in cross-section and which runs around the perimeter of each electrode plate, eliminating current from the edges. Also the backs of the outside electrode plates are insulated with polypropylene, eliminating current from these locations. The stack has 5 electrode pairs and it is run in a corrosion-resistant pressure vessel. The temperature is 30° C. and the electrolyte enters at 100 psig.

The reactor operates with 17.5 volts across the stack and the current density is 2,500 A/m². The anodes yield the following product relative to the current: $O_2$ 20%, propylene oxide 76%, propylene glycol 4%. The cathodes yield the following products relative to the current: propylene oxide 80%, water 10%, oxygen 10%.

Example 5—Bipolar Stack Array/Flowing Electrolyte/Liquid Propylene Feed

This example is similar to Example 1, with the exceptions that liquid propylene is fed with the electrolyte at 20 vol % and the reactor pressure is 220 psig. Similar results are obtained.

Example 6—Bipolar Stack Array/Intra-Cathode Oxygen Feed/Liquid Propylene Feed This example is similar to Example 2, with the exceptions that liquid propylene is substituted for the propylene solution and the reactor pressure is 220 psig. Similar results are obtained.

Example 7—Bipolar Stack Array/Extra-Cathode Oxygen Feed/Liquid Propylene Feed This example is similar to example 3, with the exceptions that liquid propylene, with 2 vol % oxygen, is substituted for the propylene solution and the reactor pressure is 220 psig. Similar results are obtained.

Example 8—Bipolar Stack Array/Flowing Electrolyte/Propylene-Permeable Anodes/Liquid Propylene Feed This example is similar to Example 4, with the exception that liquid propylene is fed with the electrolyte at 20 vol %, liquid propylene is fed to the anode gas feed channel and the reactor is at 220 psig. Similar results are obtained.

Example 9—Bipolar Stack With Carbon Cathodes and Nickel Anodes

Figure 6:
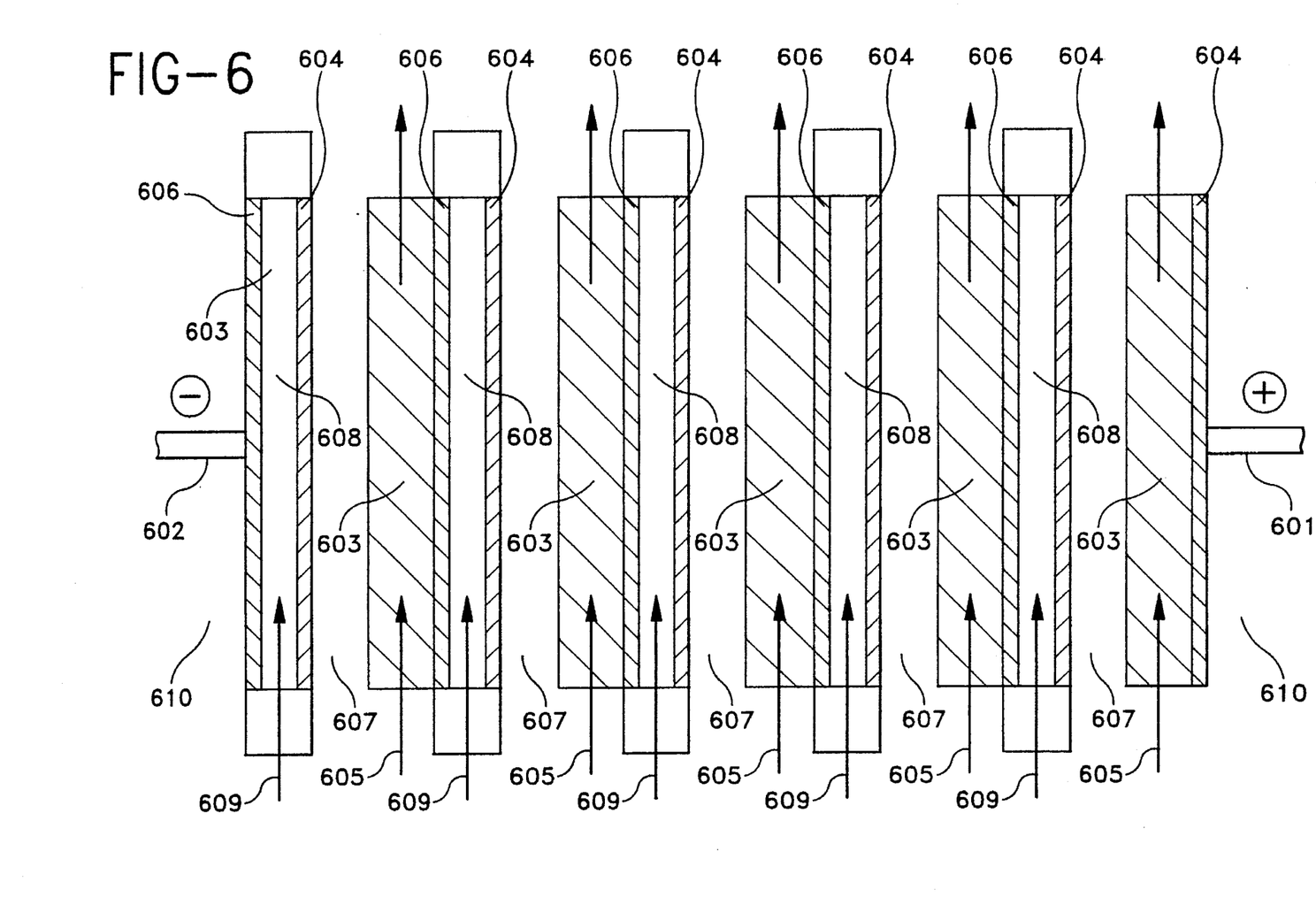
FIG. 6 illustrates practice of the invention with a bipolar stack array and continuously flowing electrolyte.

FIG. 6 illustrates another practice of the invention with a bipolar stack array and continuously flowing electrolyte. Referring to FIG. 6, electrical connections 601 and 602 are provided which are connected respectively to an external positive DC terminal and an external negative DC terminal. Each bipolar unit comprises an anode 603 and a cathode 604.

The anode is a 3-dimensional electrode nickel foam, having a high active to apparent surface area ratio and an open pore structure, presenting significant area on which the electrochemistry occurs and ready access to the electrode area by the fed electrolyte 605 and the cofed propylene gas. One face of the anode contacts the flowing electrolyte flow channel and the other is tack welded to a solid nickel plate 606. The anodes are prepared for operation by applying a negative, cathodic voltage to them at 0.05 volts in excess of that required to first discharge hydrogen gas and this potential is applied for 40 minutes. During this time the applied potential of the stack is temporarily the reverse of that which is normally applied to manufacture propylene oxide.

The cathode is of uncatalyzed carbon i.e. carbon essentially free of contaminants and it is in the form of a porous, gas diffusion electrode. One cathode face is immersed in the flowing electrolyte 607 and the other face contacts a gas feed channel 608, to which 80 vol % propylene/20 vol % oxygen 609 is continuously supplied. The cathode feed gas, containing two reactants and the electrolyte, sustaining current, must have access to the same element of cathode surface in order for the reaction to proceed. The "gas diffussion" concept is that the gas and liquid have a multitude of interfaces in the cathode pores and the solid electrode is wetted by the electrolyte. the gas has a very short path (1 to 1000 microns) through which to diffuse to the cathode surface. The specific surface area of the cathode is a large multiple (10 to 1000) of the apparent area, promoting the reaction rate. There is significant mutual feed gas/electrolyte liquid/electrode solid contact in the cathode.

The electrodes are 3 ft.wide and 6 ft. long, the electrolyte flowing parallel to the longer dimension. The nickel foam and the nickel plate to which it is tack-welded are each 3 mm thick. The cathode is 4 mm thick and the cathode gas feed channel is 3 mm thick. The cathode gas feed channel is formed of 316 stainless steel mesh of 35% open area, permitting gas flow; the mesh is in contact with the cathode and the nickel plate to which the anode is attached, providing mechanical support and electrical connection between them.

Polypropylene electrical insulation is incorporated as a strip around the periphery of each anode/cathode pair, with a slot for the cathode gas feed. The insulation essentially eliminates currents from the edges of the stack. The bipolar stack is surrounded over its 6 ft. length by polypropylene insulation 610, which extends to the vessel wall. Thus electrical currents and electrolyte flow are confined within the stack.

The electrolyte is 10 wt % dipotassium monohydrogen phosphate in water, saturated with propylene. It is cofed with gaseous propylene with the gas occupying 20 vol %. The mixture is pumped into the channels between the electrodes and flows through the stack at a mean velocity of 2 ft/s.

Every electrode pair of the reactor is polarized through polarization of the electrodes at the outside of the stack.

At each anode, water is electrolyzed and the surface-associated oxygen which forms reacts with propylene from the propylene and electrolyte mixture, yielding propylene oxide. The protons formed at the anode readily diffuse across the narrow inter-electrode gap (2 mm) to the cathode and are there reacted with oxygen and propylene at or near the gas/electrolyte/cathode interface. Propylene dissolved in the electrolyte from the feed, or that dissolved from the propylene/oxygen cathode gas channel feed, reacts to form propylene oxide and reform the water which was consumed by electrolysis. Overall, the salt and solvent of the electrolyte are essentially conserved. The propylene oxide product dissolves in the exit electrolyte and gas streams and it is removed by distillation.

The illustrated reactor has 5 electrode pairs and is run in a corrosion resistant pressure vessel. The temperature is 40° C. and the electrolyte is fed at 125 psig.

The reactor operates with 17.5 volts applied across the stack and the current density is 2500 A/m$^2$. The anodes yield the following products relative to the current: propylene oxide 80%, $O_2$ 16%, propylene glycol 4%. The cathodes yield the following products relative to the current: propylene oxide 80%, water 10%, oxygen 10%.

Example 10 Monopolar Stack with Carbon Cathodes and Nickel Anodes

This example is similar to example 9, with the exception that the electrodes are individually polarized by external application of voltage. See FIG. 7. A pair of carbon gas diffusion cathodes 604 is separated by a gas feed channel 608 and each cathode faces an anode 603. The nickel foam anodes are tacked-welded to both faces of a nickel plate 606, providing mechanical reinforcement. All other functions, dimensions and compositions are as in example 9. This example includes the anode preparation by application of negative voltage described in Example 9.

Figure 7:
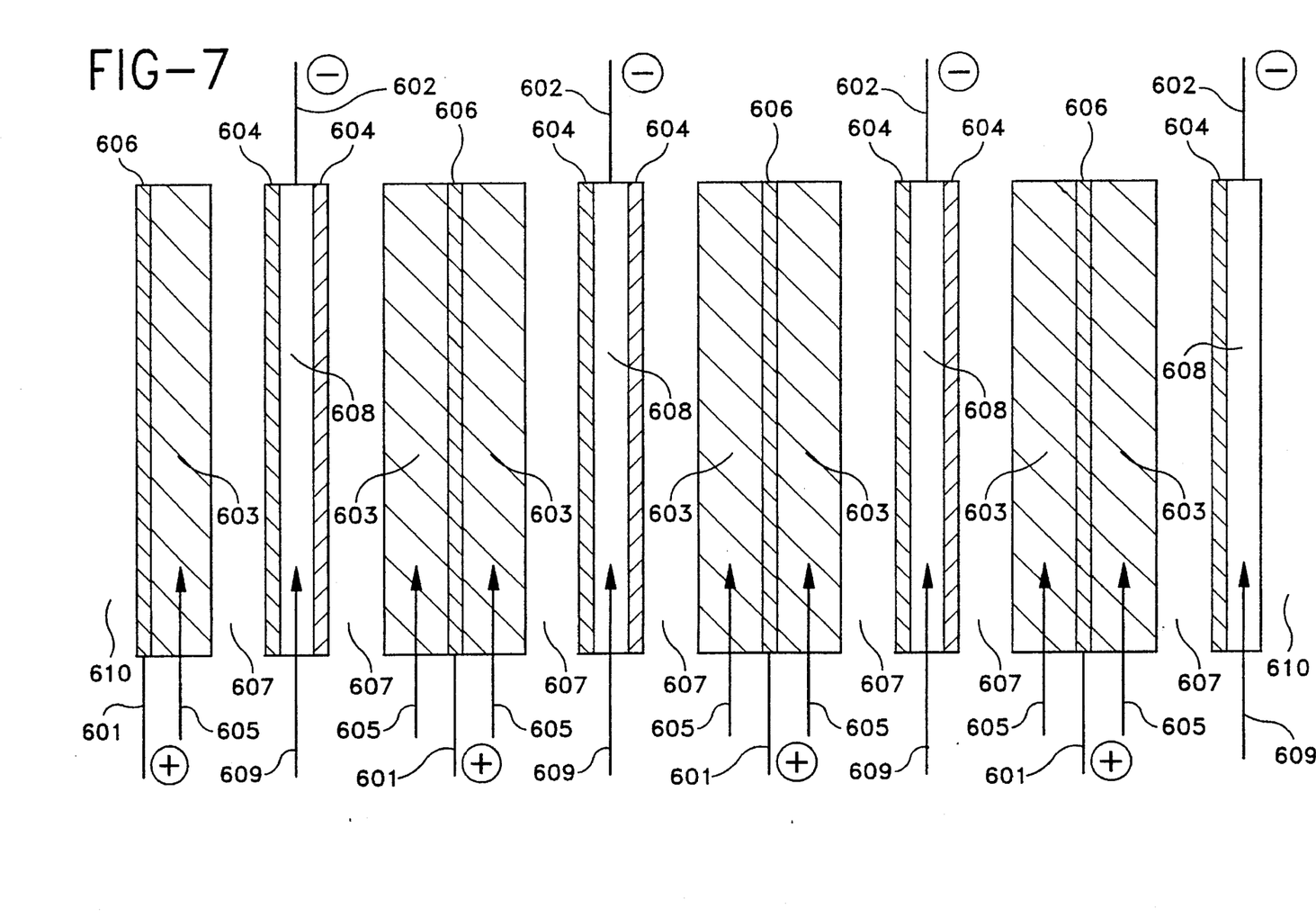
FIG. 7 illustrates practice of the invention with electrodes which are individually polarized by external application of voltage.

The illustrated reactor has 9 anodes and an equal number of cathodes and it is in a corrosion resistant pressure vessel. The temperature is 30° C. and the electrolyte is fed at 100 psig.

The reactor operates with 4 volts between the anodes and the cathodes; the current density is 3000 A/m$^2$. The anodes yield the following products relative to the current: propylene oxide 82%, $O_2$ 14%, propylene glycol 4%. The cathodes yield the following products relative to the current: propylene oxide 80%, water 10%, $O_2$ 10%.

Example 11 Bipolar Stack with Carbon Cathodes and Nickel Anodes and Intra-Electrode Gas Feed to Both Electrodes This example is similar to example 10, with the exception that the anode is fed gas similarly but separately from the cathode. A gas feed channel and a gas feed distributor are incorporated between the nickel plate separating the anode from the cathode gas feed channel. The gas feed channel is defined by nickel mesh of 50% open area and the gas distributor is porous sintered nickel. The anode gas feed is 100% propylene. The mesh allows ready access of the propylene to entire area of the anode and porous sintered nickel distributes the propylene uniformly into the interstices of the nickel foam anode. All other functions, dimensions and compositions are as in example 9. This example includes the anode preparation by application of negative voltage described in example 9.

Example 12 Bipolar Stack with Carbon/Titanium Silicalite Cathodes and Nickel Anodes This example is similar to example 9, with the exception of the cathode is 10 wt % titanium silicalite and 90 wt % carbon. All other functions,dimensions and compositions are as in example 9. This example includes the anode preparation by application of negative voltage described in example 9.

Figure 8:
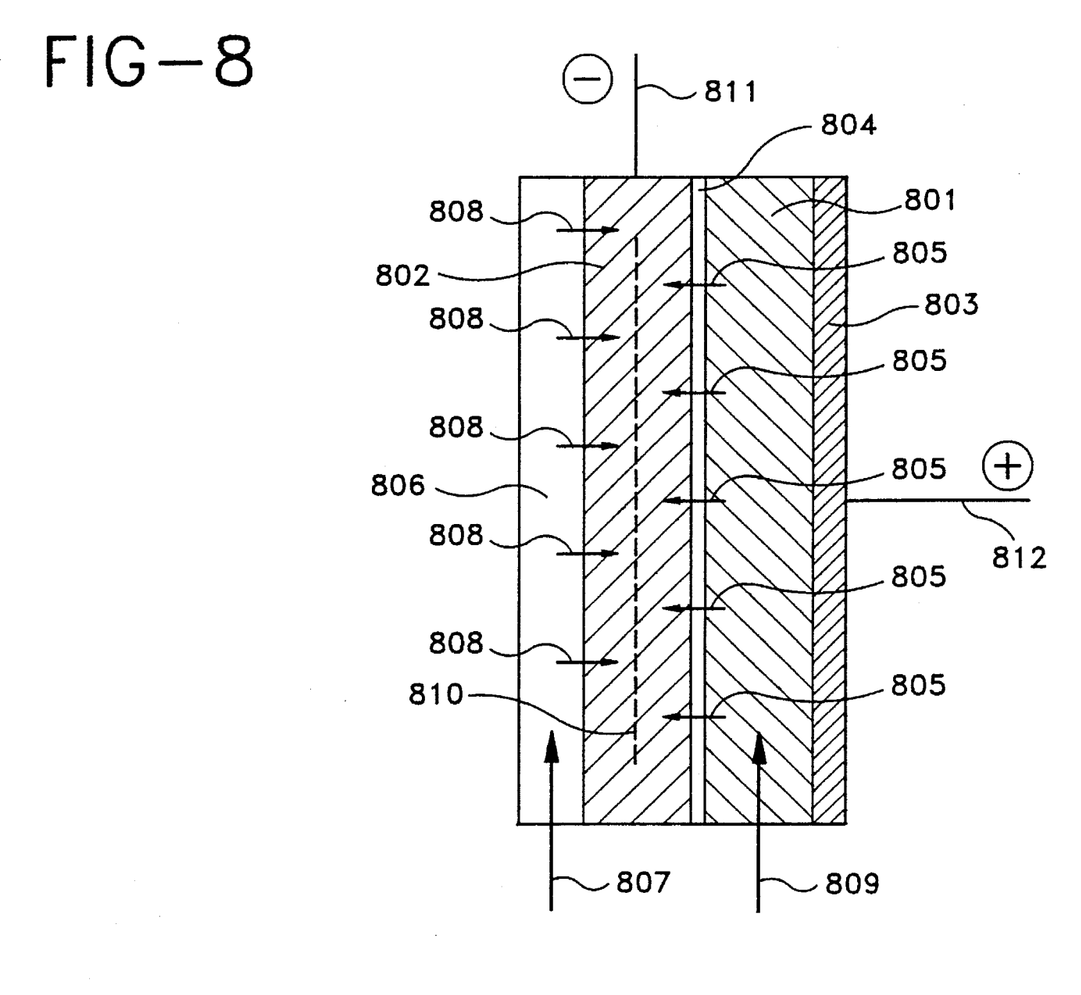
FIG. 8 illustrates practice of the invention with electrolyte flow arranged to utilize anodic oxygen at the cathode.

Example 13 Cell with Carbon Cathode and Nickel Anode with Electrolyte Pumping to Utilize Anodic Oxygen at Cathode While synthesizing Propylene Oxide at Both Electrodes FIG. 8 illustrates this example. It consists of a 3-dimensional nickel foam anode 801 and a porous cathode 802 of granular carbon and binder. The anode is tack-welded to a nickel plate 803 and it is separated from the cathode by a perforated polypropylene distributor 804 through which the analyte 805 is continuously pumped into the porous cathode, where it is the catholyte. The distributor electrolyte flow resistivity fall monotonically from bottom to top, yielding a near-uniform flow of electrolyte from the anode to the cathode on a unit area basis. The cathode is backed by a gas distributor 806 for a 75 vol % propylene/25 vol % oxygen feed 807, which enters the cathode 808 opposite the electrolyte permeation plane. The arrangement shown in FIG. 8 is repeated 50 times to yield an electrode stack which is operated in the bipolar mode. The anodes are prepared for operation by applying a negative, cathodic voltage to them at 0.05 volts in excess of that required to first discharge hydrogen gas and this potential is applied for forty minutes.

During this time the applied potential of the stack is temporarily the reverse of that which is normally applied to manufacture propylene oxide.

The nickel plate 803 is 3 mm thick, the foam 801 is 5 mm thick, the distributor 804 is 3 mm thick and the carbon cathode 802 is 10 mm thick. The cathode gas feed channel 806 is 5 mm wide.

The electrolyte feed 809 is 10 wt % dipotassium monohydrogen phosphate in water, mixed with gaseous propylene at 10 vol %. It is fed at 3 ft/s into the anode compartment, where the water of the electrolyte is oxidized to oxygen, which oxidizes propylene to propylene oxide. The anode current is distributed as follows: propylene oxide 80%, propylene glycol 4% and $O_2$ 16 vol %. The anolyte and the anodic products are continuously pumped through the distributor into the porous cathode. There the protons produced at the anode and both the oxygen supplied by the cathode gas feed and the otherwise waste oxygen gas from the anode react with electrons to yield hydrogen peroxide or peroxide. This in turn reacts with the propylene in the electrolyte and from the cathodes gas feed to yield propylene oxide. The cathode products are as follows relative to the cathode current: propylene oxide 90%, oxygen 5%, water 5%.

The equations which are believed to take place in carrying out the invention are as follows.

At the anode:

(1) $H_2O \rightarrow 2e + 2H^+ + O$ (2) $O + Olefin \rightarrow Alkylene\ Oxide$ At the cathode:

(3) $O_2 + 2e + 2H+ \rightarrow H_2O_2$ (4) $H_2O_2 + olefin \rightarrow Alkylene\ oxide + H_2O$

We claim:

1. The process for the production of alkylene oxide in an electrochemical reactor having an anode and a cathode, wherein aqueous electrolyte is electrolyzed at the reactor anode to form oxygen and protons, the said oxygen is reacted at the anode with olefin to form alkylene oxide, the protons formed at the anode are transferred from the anode to the cathode and at the cathode are contacted with oxygen and olefin at reaction conditions to form alkylene oxide.

2. The process of claim 1 wherein the alkylene oxide formed at the anode and cathode is propylene oxide.

3. The process of claim 1 wherein a dipotassium monohydrogen phosphate electrolyte is employed.

4. The process of claim 1 wherein a disodium monohydrogen phosphate electrolyte is employed.

5. The process of claim 1 wherein an electrolyte is employed which contains a water miscible organic propylene solubilizing agent.

6. The process of claim 1 wherein an electrolyte is employed which contains a $C_4$–$C_{12}$ tertiary alcohol.

7. The process of claim 1 wherein an electrolyte is employed which contains tertiary butyl alcohol.

8. The process of claim 1 wherein a nickel oxide is employed.

9. The process of claim 1 wherein a carbon cathode is employed.

10. The process of claim 1 wherein alkylene oxide formation is carried out at 10°–100° C.

* * * * *

UNITED STATES PATENT AND TRADEMARK OFFICE
CERTIFICATE OF CORRECTION

PATENT NO. : 5,527,436
DATED : June 18, 1996
INVENTOR(S) : Cooker et al

It is certified that error appears in the above-identified patent and that said Letters Patent is hereby corrected as shown below:

On the title page: Item [54] and Column 1, line 1, insert therefor --ALKYLENE--.

Signed and Sealed this

Sixth Day of January, 1998

Attest:

BRUCE LEHMAN

*Attesting Officer*   *Commissioner of Patents and Trademarks*